United States Patent
Landreville et al.

(10) Patent No.: US 6,685,741 B2
(45) Date of Patent: Feb. 3, 2004

(54) INTRAOCULAR LENSES

(75) Inventors: Michael T. Landreville, New Port Coast, CA (US); Donald Carrol Stenger, Anaheim Hills, CA (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/364,225

(22) Filed: Jul. 29, 1999

(65) Prior Publication Data

US 2002/0103536 A1 Aug. 1, 2002

(51) Int. Cl.$^7$ .................................................. A61F 2/16
(52) U.S. Cl. ..................................... 623/6.37; 623/6.44
(58) Field of Search ........................... 623/6.37, 6.11, 623/6.22, 6.43, 6.44, 6.48, 6.49, 6.38, FOR 105

(56) References Cited

U.S. PATENT DOCUMENTS

| | | |
|---|---|---|
| 5,047,051 A | 9/1991 | Cumming |
| 5,180,390 A | 1/1993 | Drews |
| 5,326,347 A | 7/1994 | Cumming |
| 5,326,506 A | 7/1994 | Vanderbilt |
| 5,476,514 A | 12/1995 | Cumming |
| 5,496,366 A | 3/1996 | Cumming |
| 5,578,081 A * | 11/1996 | McDonald .................. 623/6.17 |
| 5,674,282 A | 10/1997 | Cumming |
| 5,702,441 A | 12/1997 | Zhou |
| 6,013,101 A * | 1/2000 | Israel .......................... 623/6.43 |
| 6,228,115 B1 * | 5/2001 | Hoffmann et al. .......... 623/6.49 |

FOREIGN PATENT DOCUMENTS

| | | | | |
|---|---|---|---|---|
| JP | 07222760 A | | 8/1995 | |
| JP | 11-47168 A | * | 2/1999 | ........ 623/FOR 105 |
| WO | WO 95/06446 | * | 3/1995 | ............. A61F/2/16 |
| WO | WO 9717915 A | | 5/1997 | |
| WO | WO 9743984 A | | 11/1997 | |
| WO | WO 9856315 A | | 12/1998 | |

* cited by examiner

Primary Examiner—David H. Willse
(74) Attorney, Agent, or Firm—Rita D. Vacca

(57) ABSTRACT

An accommodating intraocular lens including an optic portion having an outer peripheral edge and two, three or four balanced haptic elements for use to achieve multifocal refractive correction. Each haptic element is formed to have less resistance to bending in a plane generally parallel to an eye's optical axis than in a plane generally perpendicular to the eye's optical axis. The intraocular lens is designed with specific flexibility characteristics so as to exhibit greater than approximately 1.0 mm axial displacement of the optic portion along the eye's optical axis under a compression force suitable to effect a 1.0 mm in diameter compression of the intraocular lens.

16 Claims, 7 Drawing Sheets

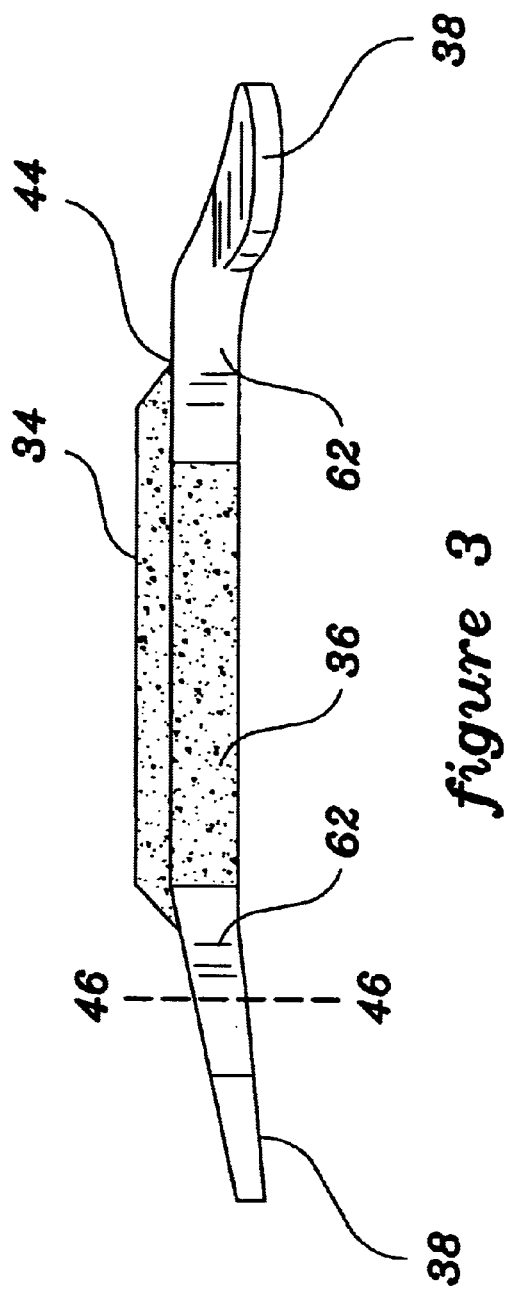
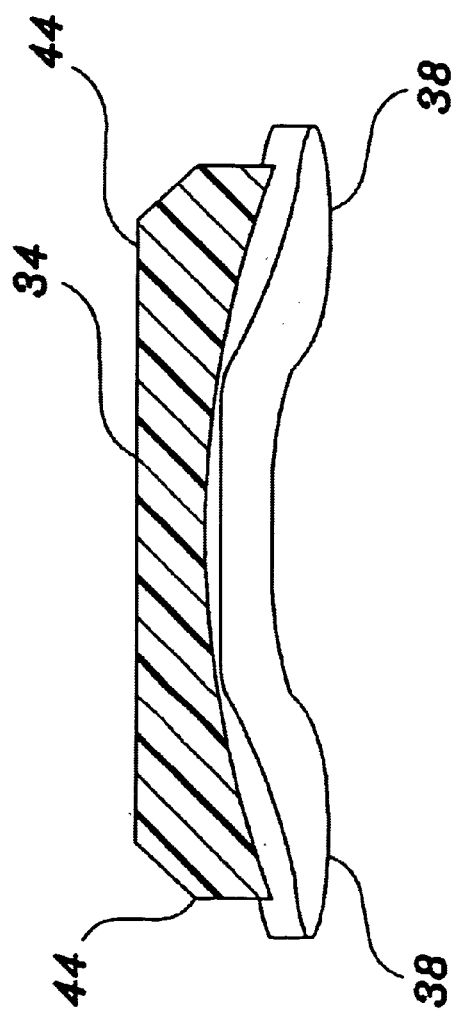

INTRAOCULAR LENSES

FIELD OF THE INVENTION

The present invention relates to intraocular lenses (IOLs) and a method for making and using the same. More particularly, the present invention relates to accommodating IOLs designed for refractive correction in aphakic eyes where a diseased natural lens is surgically removed, such as in the case of cataracts.

BACKGROUND OF THE INVENTION

IOL implants have been used for many years in aphakic eyes as replacements for diseased natural crystalline lenses that have been surgically removed from the eyes. Many different IOL designs have been developed over past years and proven successful for use in aphakic eyes. Successful IOL designs to date primarily include an optic portion with supports therefor, called haptics, connected to and surrounding at least part of the optic portion. The haptic portions of an IOL are designed to support the optic portion of the IOL in the lens capsule, anterior chamber or posterior chamber of an eye.

Commercially successful IOLs have been made from a variety of biocompatible materials, ranging from more rigid materials such as polymethylmethacrylate (PMMA) to softer, more flexible materials capable of being folded or compressed such as silicones, certain acrylics, and hydrogels. Haptic portions of the IOLs have been formed separately from the optic portion and later connected thereto through processes such as heat, physical staking and/or chemical bonding. Haptics have also been formed as an integral part of the optic portion in what is commonly referred to as "single-piece" IOLs.

Softer, more flexible IOLs have gained in popularity in more recent years due to their ability to be compressed, folded, rolled or otherwise deformed. Such softer IOLs may be deformed prior to insertion thereof through an incision in the cornea of an eye. Following insertion of the IOL in an eye, the IOL returns to its original pre-deformed shape due to the memory characteristics of the soft material. Softer, more flexible IOLs as just described may be implanted into an eye through an incision that is much smaller, i.e., 2.8 to 3.2 mm, than that necessary for more rigid IOLs, i.e., 4.8 to 6.0 mm. A larger incision is necessary for more rigid IOLs because the lens must be inserted through an incision in the cornea slightly larger than the diameter of the inflexible IOL optic portion. Accordingly, more rigid IOLs have become less popular in the market since larger incisions have been found to be associated with an increased incidence of postoperative complications, such as induced astigmatism.

After IOL implantation, both softer and more rigid IOLs are subject to compressive forces exerted on the outer edges thereof from natural brain-induced contraction and relaxation of the ciliary muscle and increases and decreases in vitreous pressure. Compressive forces of this kind are useful in a phakic eye for focusing the eye at various distances. Most commercially successful IOL designs for use in aphakic eyes have single focus optic portions that are fixed and focus the eye at only a certain fixed distance. Such single focus IOLs require the wearing of glasses to change the focus of the eye. A few bifocal IOLs have been introduced to the commercial market but suffer from the disadvantage that each bifocal image represents only about forty percent of the available light and the remaining twenty percent of the light is lost to scatter, which provides lessened visual acuity.

Because of the noted shortcomings of current IOL designs, there is a need for accommodating IOLs designed to provide multifocal visual imaging in aphakic eyes without the aid of eyeglasses.

SUMMARY OF THE INVENTION

An accommodating intraocular lens (IOL) made in accordance with the present invention has an optic portion with an outer peripheral edge and two, three or four haptic elements for supporting the optic portion in a patient's eye. A lens having two haptic elements is balanced by having a haptic element formed or attached on two opposed edges of the optic portion. A lens having three haptic elements is balanced by having a set of two haptic elements formed or attached on one edge of the optic and the third haptic element formed or attached on an opposite edge of the optic. A lens having four haptic elements is balanced by having a set of two haptic elements formed or attached on one edge of the optic and a set of two haptic elements formed or attached on an opposite edge of the optic. Each haptic element has an attachment portion that permanently connects the haptic element to the outer peripheral edge of the optic portion. If the haptic element is of a looped design, the haptic element has generally two attachment portions that permanently connect the looped haptic element to the outer peripheral edge of the optic portion. In the case of lenses having three or four looped haptic elements, a set of two looped haptic elements may have three attachment portions rather than four. In such a case, one of the three attachment portions is common to each of the two looped haptic elements in the set. Each haptic element whether of a loop design or not includes a flexible central portion located between the attachment portion and a contact plate. The contact plate is designed to engage an inner surface of a patient's eye. The flexible central portions that extend between the contact plates and the attachment portions allow the optic portion of the lens to move or to adjust to pressures exerted on the lens within the eye. Additionally, within these flexible central portions, each haptic element is designed to have less resistance to bending in a plane generally parallel to the optical axis of an eye than in a plane generally perpendicular to the optical axis of an eye. By providing haptic elements with this type of flexibility characteristic, the present IOL maximizes axial displacement of the optic portion along the optical axis of the eye when compressive forces are exerted against the IOL. By increasing the subject IOLs movement along the optical axis of an eye, multifocal visual imaging without the aid of eyeglasses is achieved.

Accordingly, it is an object of the present invention to provide accommodating intraocular lenses for use in aphakic eyes.

Another object of the present invention is to provide accommodating intraocular lenses for use in aphakic eyes, which maximize axial displacement of the optic portions of the lenses along the optical axis of the eyes.

Another object of the present invention is to provide accommodating intraocular lenses for use in aphakic eyes, which minimize damage to tissues in the interior of the eyes.

Still another object of the present invention is to provide accommodating intraocular lenses, which are resistant to decentration within the eyes.

These and other objectives and advantages of the present invention, some of which are specifically described and others that are not, will become apparent from the detailed description, drawings and claims that follow, wherein like features are designated by like numerals.

BRIEF DESCRIPTION OF THE DRAWINGS

FIG. 3 is a side view of the IOL of FIG. 2;

FIG. 4 is a cross sectional view of the IOL of FIG. 2 taken along line 4—4;

DETAILED DESCRIPTION OF THE INVENTION

Figure 1:
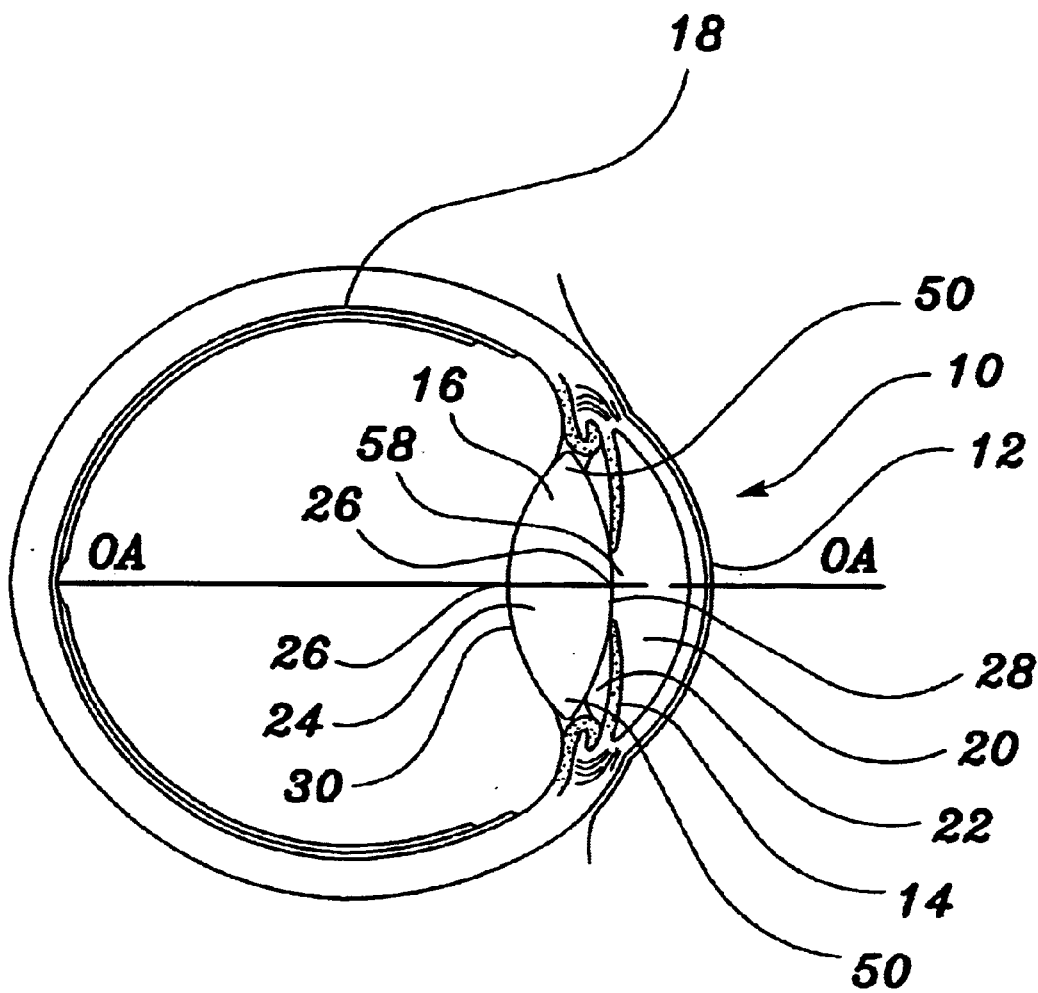
FIG. 1 is a schematic representation of the interior of a human eye.

FIG. 1 illustrates a simplified diagram of an eye 10 showing landmark structures relevant to the implantation of an intraocular lens of the present invention. Eye 10 includes an optically clear cornea 12 and an iris 14. A natural crystalline lens 16 and a retina 18 are located behind the iris 14 of eye 10. Eye 10 also includes anterior chamber 20 located in front of iris 14 and a posterior chamber 22 located between iris 14 and natural lens 16. Accommodating IOLs of the present invention are preferably implanted in lens capsule 24 after the removal of diseased natural lens 16 (aphakic application). When used in aphakic eyes, IOLs serve as replacements for surgically removed diseased natural lenses 16, such as for example following cataract surgeries. Eye 10 also includes an optical axis OA—OA that is an imaginary line that passes through the optical center 26 of anterior surface 28 and posterior surface 30 of lens 16. Optical axis OA—OA in the human eye 10 is generally perpendicular to a portion of cornea 12, natural lens 16 and retina 18.

Figure 2:
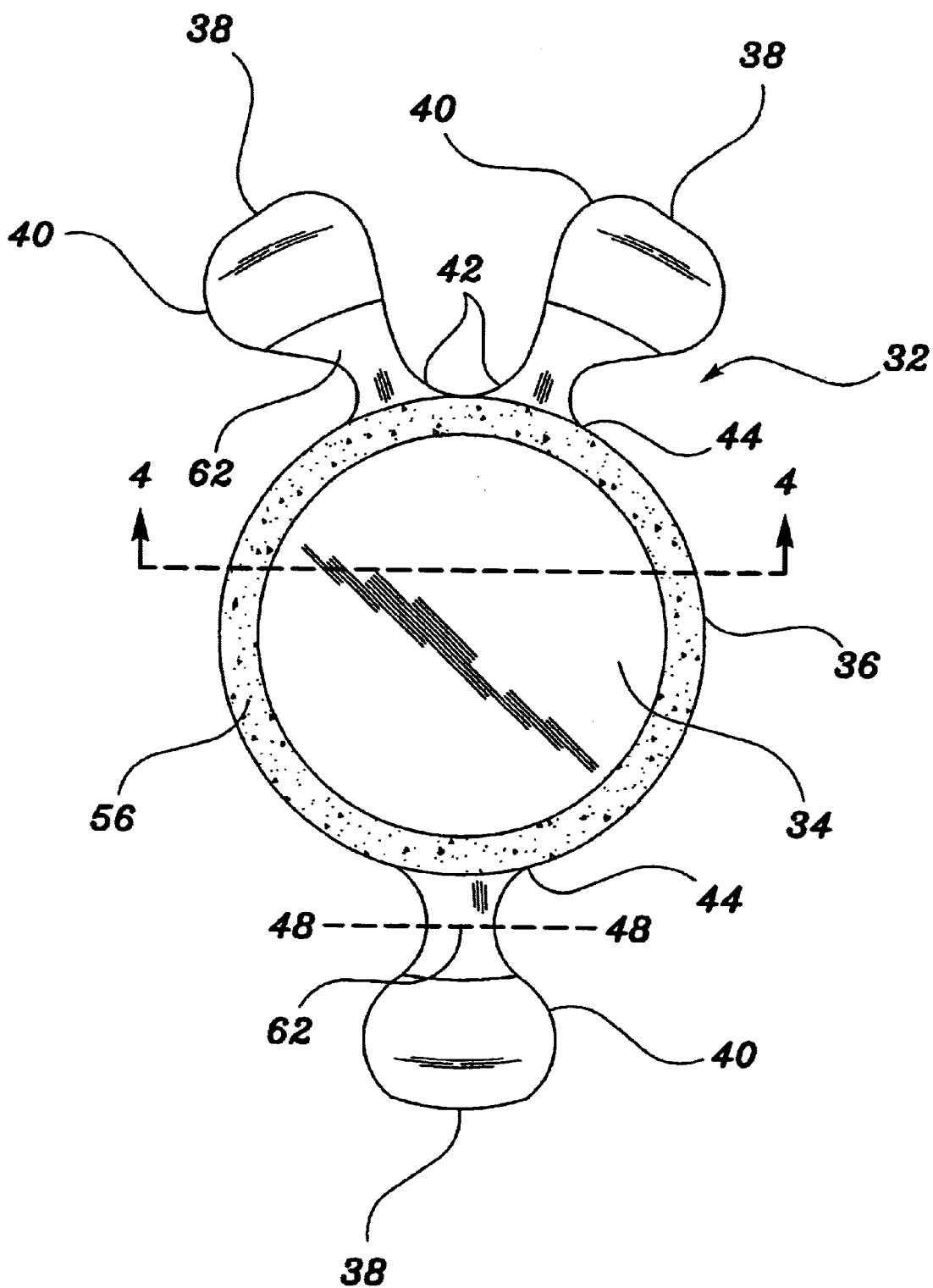
FIG. 2 is a plan view of an IOL with three haptics made in accordance with the present invention.
Figure 5:
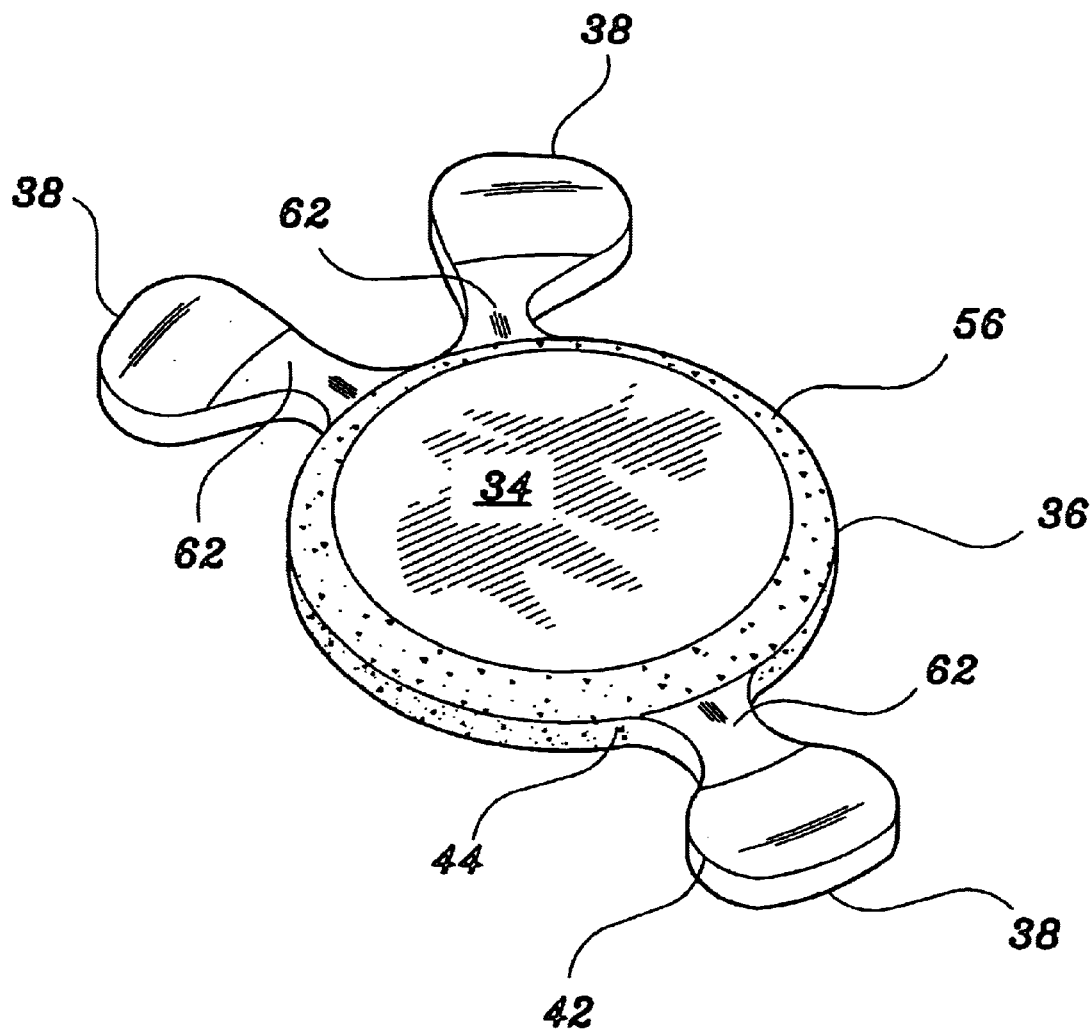
FIG. 5 is a perspective view of the IOL of FIG. 2.
Figure 7:
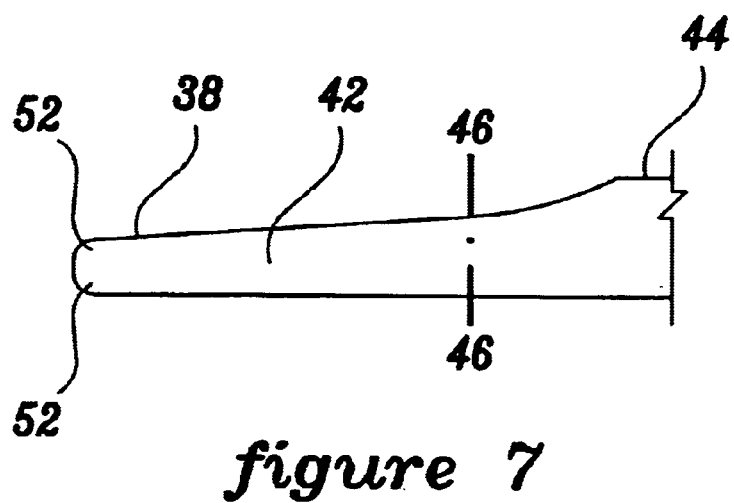
FIG. 7 is a side view of the haptic element of FIG. 3 with rounded edges.
Figure 8:
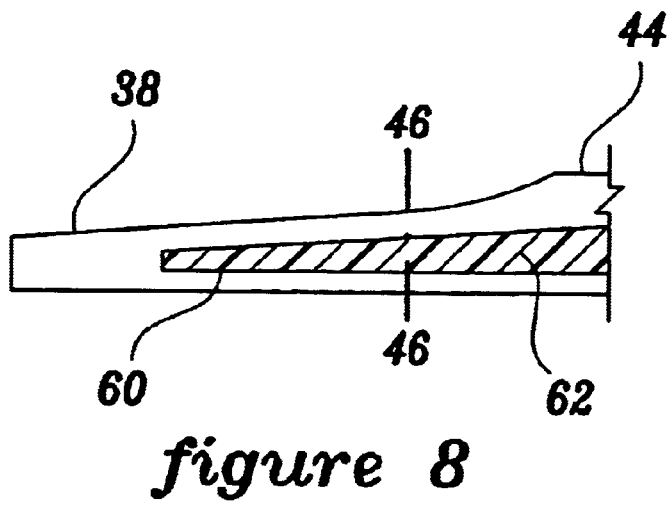
FIG. 8 is a cross sectional view of the haptic element of FIG. 6 with a stiffening element.
Figure 9:
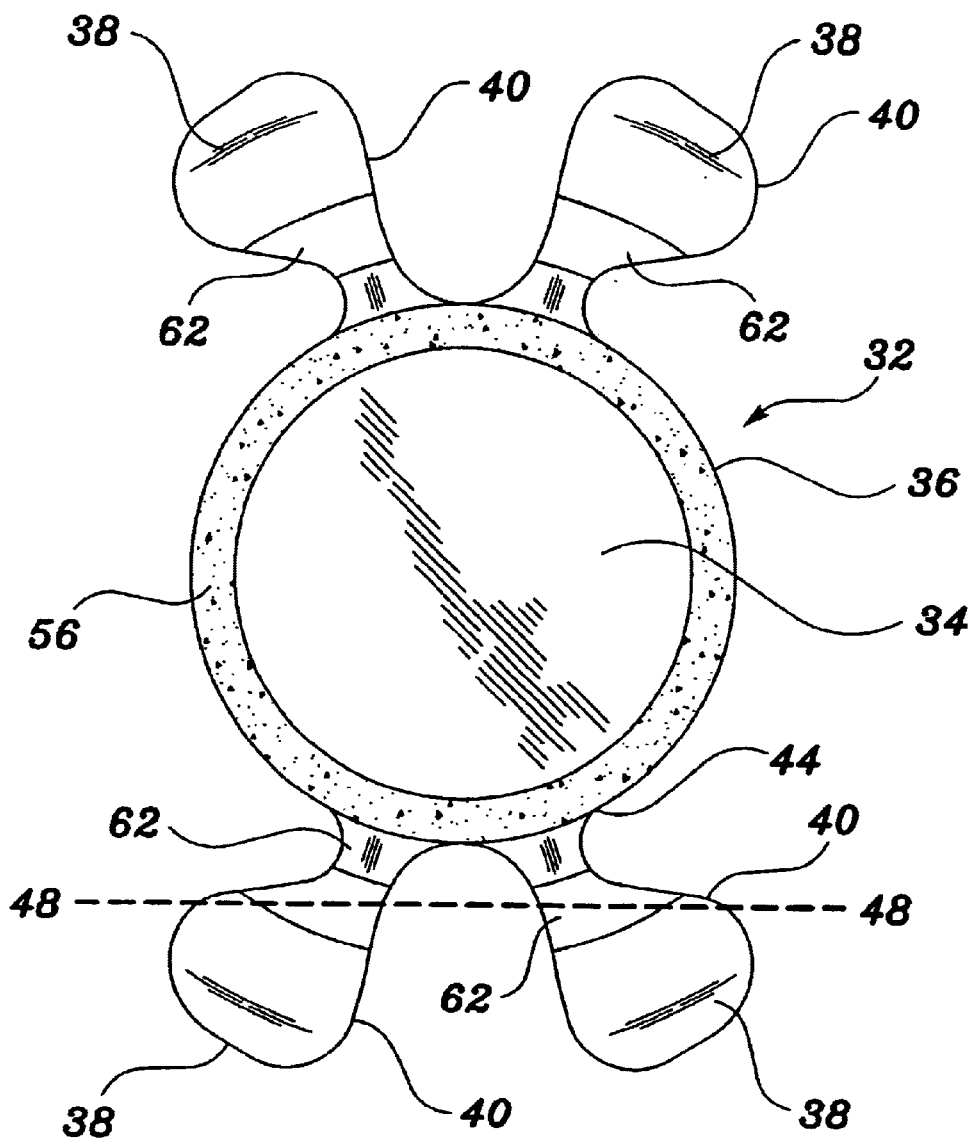
FIG. 9 is a plan view of an IOL with four haptics made in accordance with the present invention.
Figure 10:
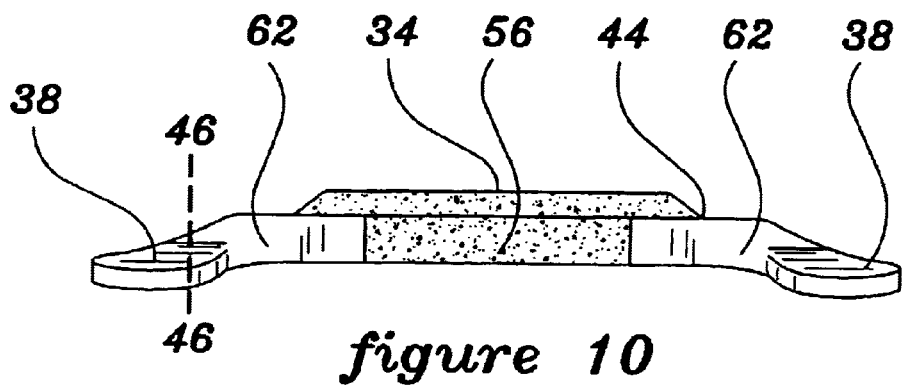
FIG. 10 is a side view of the IOL of FIG. 9.
Figure 11:
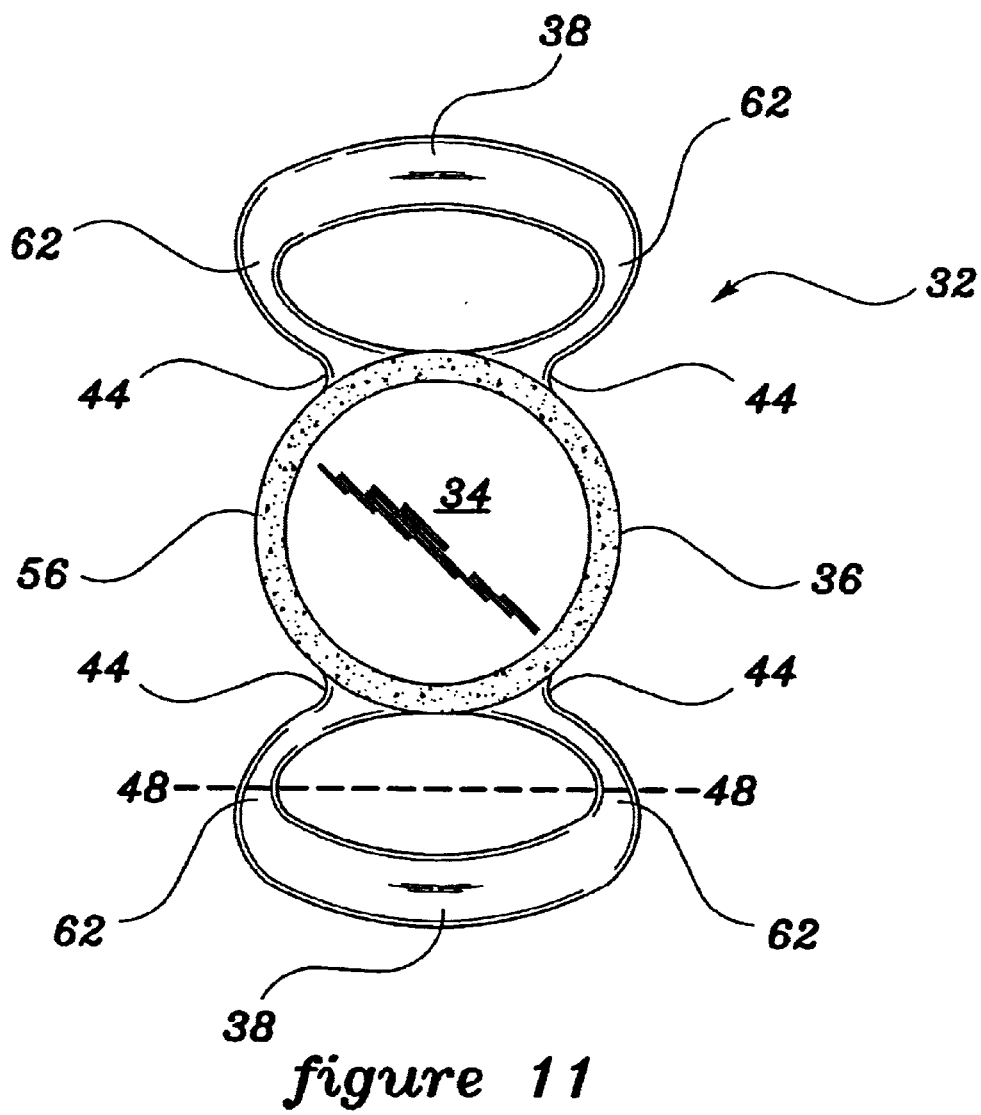
FIG. 11 is a plan view of an IOL with two haptics made in accordance with the present invention.

The IOL of the present invention, as illustrated in FIGS. 2 through 12 but best illustrated in FIGS. 2, 9 and 11, is identified generally by reference numeral 32. IOL 32 has an optic portion 34 with an outer peripheral edge 36. IOL 32 is designed for implantation preferably in lens capsule 24 of a patient's eye 10 and is preferably vaulted. A vault of approximately 1.0 to 2.0 mm but preferably 1.6 to 1.7 mm measuring from the plane of outer peripheral edge 36 of optic portion 34 to the plane of contact plates 38, described in detail below, is generally suitable. Preferably integrally formed on peripheral edge 36 of optic portion 34 are two, three or four looped or non-looped haptic elements 40, each having an edge portion 42. Haptic elements 40 are preferably integrally formed with and permanently connected to outer peripheral edge 36 of optic portion 34 by attachment portions 44. Alternatively however, haptic elements 40 may be attached to optic portion 34 by staking, chemical polymerization or other methods known to those skilled in the art. Each haptic element 40 also includes a broadened contact plate 38 designed to preferably engage inner surfaces 50 in lens capsule 24 of eye 10.

In accordance with the present invention, haptic elements 40 are designed so that when IOL 32 is implanted in a patient's eye 10 and held in place through compressive forces exerted by inner surfaces 50 on contact plates 38 of haptic elements 40, haptic elements 40 flex so that contact plates 38 do not slide along surfaces 50 in eye 10. Accordingly, haptic elements 40 are designed to flex in a plane generally perpendicular to that of optic portion 34 of IOL 32 and generally parallel to that of optical axis OA—OA of eye 10. By designing this type of flexibility characteristic into haptic elements 40, IOL 32 allows an eye to achieve multifocal visual imaging without the aid of eyeglasses. The flexibility characteristic of haptic elements 40 maximizes axial displacement of optic portion 34 in a direction along optical axis OA—OA of eye 10. Compressive forces of differing magnitudes within the range of approximately 0.1 to 5 mN exerted against contact plates 38 of haptic elements 40 to effect approximately an overall 1.0 mm in diameter compression of IOL 32, such as that caused by natural brain-induced forces within eye 10, results in more than approximately 1.0 mm, but more preferably more than approximately 1.5 mm and most preferably more than approximately 2.0 mm axial displacement of optic portion 34 along optical axis OA—OA in an eye 10. The unique design of IOL 32 achieves significantly maximized axial displacement of optic portion 34. The IOL 32 of the present invention with its maximized axial displacement of optic portion 34 enables an eye to achieve multifocal visual imaging when a wide range of compressive forces, potentially even greater than those described above, are applied to eye 10.

Figure 6:
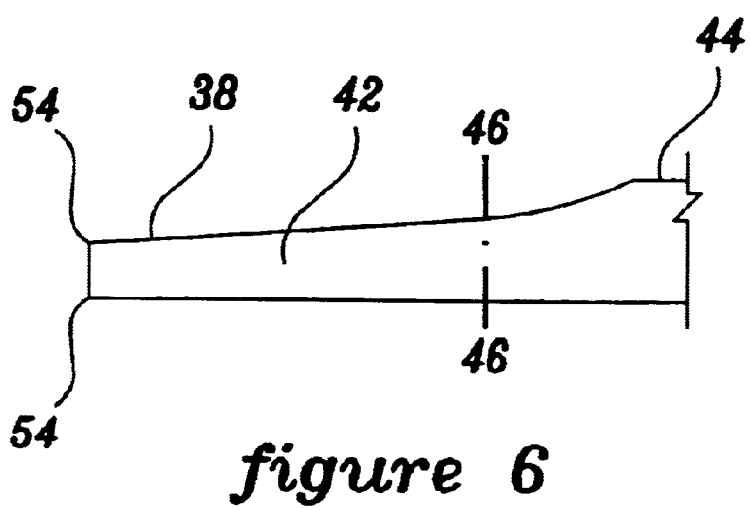
FIG. 6 is a side view of the haptic element of FIG. 3 with sharper edges.
Figure 12:
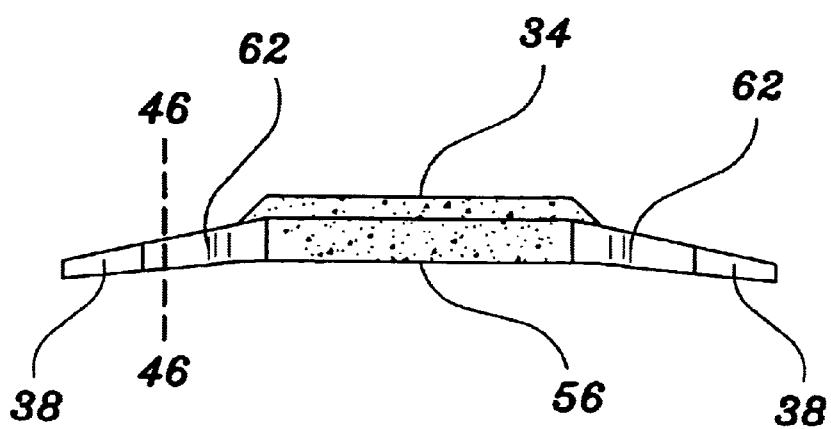
FIG. 12 is a side view of the IOL of FIG. 11.

The flexibility characteristic of haptic elements 40 of IOL 32 as described above is achieved through the unique design thereof. As best illustrated in FIG. 2, IOL 32 has haptic elements 40 formed with flexible central portions 62 adjacent to attachment portions 44 permanently connected to outer peripheral edge 36 of optic portion 34. Flexible central portions 62 are essential in imparting the necessary flexibility to the IOLs of the present invention. Flexible central portions 62 have a dimension in plane 46—46 generally parallel to optical axis OA—OA, as depicted in FIGS. 3, 10 and 12, less than or equal to but most preferably less than the same in plane 48—48 generally perpendicular to optical axis OA—OA as depicted in FIGS. 2, 9 and 11. Contact plate 38 is relatively flat with either rounded edges 52 as depicted in FIG. 7 to provide a smoother fit with inner surfaces 50, or more defined, sharper edges 54 as depicted in FIG. 6 to provide a barrier to prevent cellular migration and growth upon implantation in lens capsule 24.

The subject IOL 32 is preferably manufactured to have an optic portion 34 approximately 4.5 to 9.0 mm, but preferably approximately 5.0 to 6.0 mm and most preferably 5.5 mm in diameter and approximately 0.15 mm to 1.0 mm, but preferably approximately 0.6 to 0.8 mm and most preferably 0.7 mm in thickness at peripheral edge 36. Haptic elements 40 extend from the optic portion 34 of IOL 32 in a generally rounded or oval configuration and will increase or decrease in overall length depending upon the size of lens desired and the diameter of optic portion 34. As the diameter of optic portion 34 increases, the overall length of haptic elements 40 may be decreased. Likewise, as the diameter of optic portion 34 decreases, the overall length of haptic elements 40 may be increased. However, as customary, the overall length of the haptic elements 40 are varied to achieve desired IOL 32 sizes rather than varying the sizes of optic portions 34. In general, looped haptic elements 40 as illustrated in FIG. 11 are formed to be approximately 2.6 to 6.0 mm, but preferably approximately 3.4 to 5.0 mm and most preferably approximately 4.2 mm in length measuring from a point of equal distance between common attachment portions 44 on peripheral edge 36, to the center of contact plate 38. Looped haptic elements 40 preferably have a generally rounded or oval configuration as illustrated in FIGS. 11 and 12 to allow axial deflection under compressive forces. Non-looped haptic elements 40 as illustrated in FIGS. 2 and 9 are formed to be approximately 2.6 to 6.0 mm, but preferably approximately 3.4 to 5.0 mm and most preferably approximately 4.2 mm in length measuring from the middle of attachment portion 44 on peripheral edge 36, to the center of contact plate 38. Non-looped haptic elements 40 preferably have a generally rounded or oval configuration as illustrated in FIGS. 2 and 9 to provide a suitable stable fit within lens capsule 24 while allowing axial deflection under compressive forces. For purposes of the present invention, the generally rounded or oval shape of looped and non-looped haptic elements 40, i.e., the beam curve shape, relative to the width to thickness ratio, i.e., the aspect ratio, of haptic element 40 as described herein is critical to achieve suitable function. Flexible central portion 62 of haptic element 40 is approximately 0.5 to 2.5 mm, but preferably approximately 1.0 to 2.0 mm and most preferably 1.6 mm in length; approximately 0.2 to 1.0 mm, but preferably approximately 0.3 to 0.7 mm and most preferably approximately 0.46 mm in width in plane 48—48 and approximately 0.2 to 0.7 mm, but preferably approximately 0.3 to 0.6 and most preferably approximately 0.43 mm in thickness in plane 46—46. Contact plate 38 is approximately 0.8 to 2.5 mm, but preferably approximately 1.0 to 2.2 mm and most preferably approximately 1.8 mm in length, approximately 0.05 to 0.5 mm, but preferably approximately 0.1 to 0.4 mm and most preferably approximately 0.3 mm in thickness and approximately 0.6 to 1.5 mm, but preferably approximately 0.8 to 1.2 mm and most preferably approximately 1.0 mm in width.

As provided through the dimensions of IOL 32 above, looped and non-looped haptic elements 40 are relatively thick in plane 48—48 at contact plate 38 through to attachment portions 44 and optic portion 34, with flexible central portions 62 preferably exhibiting a thinner dimension in plane 46—46 than that of the width in plane 48—48. Looped haptic elements 40 of the subject design tend to resist deflection into closer proximity with outer peripheral edge 36 when a compression force is exerted against contact plates 38 to maximize axial displacement along optical axis OA—OA. When accommodating IOL 32 is used as a refractive lens, a stable, reliable multifocal refractive correction is provided.

The desired flexibility characteristic of haptic elements 40 of IOL 32 may likewise be achieved or enhanced by incorporating a stiffening element 60, in the shape of a wide, very thin ribbon, in one or more haptic elements 40, as illustrated in FIG. 8. Stiffening element 60 may be positioned in haptic element 40 so that wide or broad flat face 62 is oriented in a plane parallel to that of plane 48—48 so as to be thin axially in a plane parallel to that of plane 46—46. Stiffening element 60 functions in a manner similar to that of an I-beam in construction to maximize axial displacement along optical axis OA—OA when compressive force is applied to contact plates 38.

Stiffening element 60 is formed of a less flexible material than that of IOL 32. Suitable materials for stiffening element 60 include but are not limited to polyimides, polyolefins, high-density polyethylenes, polyesters, nylons, metals or any biocompatible material with suitable stiffening characteristics. Stiffening element 60 may be fabricated using one or more layers of a mesh, screen, webbing and/or sheet to impart the desired flexibility characteristics described herein. Stiffening element 60 may be used in conjunction with haptic elements 40 described above in cases where a thinner haptic design is desired while still achieving the desired stability and flexibility characteristics.

Suitable materials for the production of the subject IOL 32 include but are not limited to foldable or compressible materials, such as silicone polymers, hydrocarbon and fluorocarbon polymers, hydrogels, soft acrylic polymers, polyesters, polyamides, polyurethane, silicone polymers with hydrophilic monomer units, fluorine-containing polysiloxane elastomers and combinations thereof. The preferred material for the production of IOL 32 of the present invention is a hydrogel made from 2-hydroxyethyl methacrylate (HEMA) and 6-hydroxyhexyl methacrylate (HOHEXMA), i.e., poly(HEMA-co-HOHEXMA). Poly(HEMA-co-HOHEXMA) is the preferred material for the manufacture of IOL 32 due to its equilibrium water content of approximately 18 percent by weight, and high refractive index of approximately 1.474, which is greater than that of the aqueous humor of the eye, i.e., 1.33. A high refractive index is a desirable feature in the production of IOLs to impart high optical power with a minimum of optic thickness. By using a material with a high refractive index, visual acuity deficiencies may be corrected using a thinner IOL. Poly(HEMA-co-HOHEXMA) is a desirable material in the production of IOLs 32 due to its mechanical strength, which is suitable to withstand considerable physical manipulation. Poly(HEMA-co-HOHEXMA) also has desirable memory properties suitable for IOL use. IOLs manufactured from a material possessing good memory properties such as those of poly(HEMA-co-HOHEXMA) unfold in a more controlled manner in an eye, rather than explosively, to its predetermined shape. The unique design of the subject IOL 32 with haptic elements 40 manufactured from a material having good memory properties also provides improved control of haptic unfolding upon insertion thereof in eye 10. Explosive unfolding of IOLs is undesirable due to potential damage to delicate tissues within the eye. Poly(HEMA-co-HOHEXMA) also has dimensional stability in the eye, which is desirable.

Although the teachings of the present invention are preferably applied to soft or foldable IOLs formed of a foldable or compressible material, the same may also be applied to harder, less flexible lenses formed of a relatively rigid material such as polymethylmethacrylate (PMMA) having flexible haptics formed either of the same or a different material.

Optic portion 34 of IOL 32 can be a positive powered lens from 0 to approximately +40 diopters or a negative powered lens from 0 to approximately −30 diopters. Optic portion 34 may be biconvex, plano-convex, plano-concave, biconcave or concave-convex (meniscus), depending upon the power required to achieve the appropriate central and peripheral thickness for efficient handling.

Optic portion 34 of the subject IOL 32 may optionally be formed with a glare reduction zone 56 of approximately 0.25 to 2.00 mm but more preferably approximately 0.3 to 0.6 mm and most preferably 0.5 mm in width adjacent outer peripheral edge 36 for reducing glare when outer peripheral edge 36 of IOL 32 is struck by light entering eye 10 during high light or at other times when pupil 58 is dilated. Glare reduction zone 56 is typically fabricated of the same material as optic portion 34, but may be opaque, colored or patterned in a conventional manner to block or diffuse light in plane with optical axis OA—OA.

Subject IOL 32 may be molded or preferably manufactured by first producing disks from a material of choice as described in U.S. Pat. Nos. 5,217,491 and 5,326,506 each incorporated herein in its entirety by reference. If disks are produced, IOL 32 is then be machined from the material disks in a conventional manner. Once machined or molded, IOL 32 may be polished, cleaned, sterilized and packaged by a conventional method known to those skilled in the art.

Subject IOL 32 is used in eye 10 by creating an incision in cornea 12 and capsule 24, removing natural lens 16, inserting IOL 32 in capsule 24 and closing the incision.

IOL 32 of the present invention provides for an accommodating lens suitable for use in lens capsule 24 of eye 10. IOL 32 has haptic elements 40 with flexibility characteristics that maximize axial displacement along optical axis OA—OA of eye 10 thereby enabling an eye to achieve multifocal visual imaging without the aid of eyeglasses.

While there is shown and described herein certain specific embodiments of the present invention, it will be manifest to those skilled in the art that various modifications may be made without departing from the spirit and scope of the underlying inventive concept and that the same is not limited to the particular forms herein shown and described except insofar as indicated by the scope of the appended claims.

We claim:

1. An accommodating intraocular lens to be implanted within an eye generally perpendicular to an optical axis of the eye comprising:

an outer peripheral edge defining an optic portion, two, three or four non-filamentary haptic elements each of non-uniform thickness between an anterior surface and a posterior surface of said haptic elements and each permanently connected to said outer peripheral edge by one or more attachment portions of greatest haptic element thickness and a width greater than that of adjacent flexible central portions, flexible central portions flexible throughout in a plane parallel to said eye's optical axis and dimensioned to have greater resistance to flexing in a plane perpendicular to said eye's optical axis, unitarily formed with said attachment portions opposite said outer peripheral edge, and contact plates unitarily formed with said flexible central portions opposite said attachment portions and dimensioned to be of greater width than that of said attachment portions.

2. The intraocular lens of claim 1 wherein the haptic elements and the optic portion are both formed of a foldable or compressible material.

3. The intraocular lens of claim 1 wherein said lens is formed from a material selected from the group consisting of silicone polymers, hydrocarbon and fluorocarbon polymers, hydrogels, soft acrylic polymers, polyester, polyamides, polyurethane, silicone polymers with hydrophilic monomer units, fluorine-containing polysiloxane elastomers and combinations thereof.

4. The intraocular lens of claim 1 wherein said lens is formed from a hydrogel material.

5. The intraocular lens of claim 1 wherein said lens is formed from a hydrogel material which is 18 percent by weight water.

6. The intraocular lens of claim 1 wherein said lens is formed from poly(HEMA-co-HOHEXMA).

7. The intraocular lens of claim 1 wherein said lens is formed from a material having a refractive index above 1.33.

8. The intraocular lens of claim 1 wherein said lens is formed from an acrylic material.

9. The intraocular lens of claim 1 wherein said lens is formed from a silicone material.

10. The intraocular lens of claim 1 wherein said haptic elements are formed with a dimension in a plane generally perpendicular to the eye's optical axis to be greater than or equal to a dimension in a plane generally parallel to the eye's optical axis.

11. The intraocular lens of claim 1 wherein a glare reduction zone is formed adjacent to the outer peripheral edge of the optic portion.

12. The intraocular lens of claim 1 wherein one or more of said haptic elements includes a stiffening element having less resistance to bending in a plane generally parallel to the eye's optical axis than in a plane generally perpendicular to the eye's optical axis.

13. The intraocular lens of claim 1 wherein one or more of said haptic elements includes a stiffening element formed from a material selected from the group consisting of polyimide, polyolefin, high-density polyester, nylon and metal.

14. A method of manufacturing the intraocular lens of claim 1 comprising:

forming a disk of a suitable material, and machining said lens from said disk.

15. A method of manufacturing the intraocular lens of claim 1 comprising:

molding said lens of a suitable material.

16. A method of using the intraocular lens of claim 1 comprising:

creating an incision in a cornea and lens capsule of an eye, removing a natural lens of said eye, and inserting said intraocular lens in said lens capsule of said eye.

* * * * *

UNITED STATES PATENT AND TRADEMARK OFFICE
CERTIFICATE OF CORRECTION

PATENT NO.     : 6,685,741 B2 Page 1 of 1
DATED          : February 3, 2004
INVENTOR(S)    : Michael T. Landreville et al.

It is certified that error appears in the above-identified patent and that said Letters Patent is hereby corrected as shown below:

<u>Column 8,</u>
Line 32, replace "wherein one or more" with -- wherein the --.
Line 33, replace "of said haptic elements" with -- haptic element --.

Signed and Sealed this

Twenty-ninth Day of March, 2005

JON W. DUDAS
*Director of the United States Patent and Trademark Office*